US010932801B2

(12) United States Patent
Okada et al.

(10) Patent No.: US 10,932,801 B2
(45) Date of Patent: Mar. 2, 2021

(54) ENDOSCOPE TREATMENT TOOL

(71) Applicant: OLYMPUS CORPORATION, Tokyo (JP)

(72) Inventors: Tsutomu Okada, Tokyo (JP); Hiroyuki Morishita, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 337 days.

(21) Appl. No.: 16/037,000

(22) Filed: Jul. 17, 2018

(65) Prior Publication Data

US 2018/0317945 A1 Nov. 8, 2018

Related U.S. Application Data

(63) Continuation of application No. PCT/JP2016/065640, filed on May 26, 2016.

(51) Int. Cl.
*A61B 17/221* (2006.01)
*A61B 1/00* (2006.01)
(Continued)

(52) U.S. Cl.
CPC ........ *A61B 17/221* (2013.01); *A61B 1/00085* (2013.01); *A61B 1/00087* (2013.01);
(Continued)

(58) Field of Classification Search
CPC .............. A61B 17/221; A61B 1/00085; A61B 2017/2212; A61B 2017/2217
See application file for complete search history.

(56) References Cited

U.S. PATENT DOCUMENTS

| 4,347,846 A | 9/1982 | Dormia |
| 4,612,931 A | 9/1986 | Dormia |

(Continued)

FOREIGN PATENT DOCUMENTS

| EP | 1 516 591 A1 | 3/2005 |
| EP | 2638870 A1 | 9/2013 |

(Continued)

OTHER PUBLICATIONS

Extended Supplementary European Search Report dated Dec. 18, 2019 in European Patent Application No. 16 90 3150.7.
(Continued)

*Primary Examiner* — Tuan V Nguyen
(74) *Attorney, Agent, or Firm* — Scully, Scott, Murphy & Presser, P.C.

(57) ABSTRACT

An endoscope treatment tool includes: a sheath having a lumen; a basket section protruding from the lumen and having an elastic wire; and an operating wire. The elastic wire has: a maximum section where the outer diameter of the basket section is largest of the elastic wire; a first section that, in a lateral view from a direction orthogonal to a normal from the maximum section to the central axis of the basket section, is largest on the opposite side of the central axis from the maximum section between the maximum section and the proximal end; and a second section that is largest at a position away from the normal between the maximum section and the first section, and in the front view, the first section is located on the opposite side of a straight line orthogonal to the normal at the central axis from the maximum section side.

9 Claims, 13 Drawing Sheets

(51) Int. Cl.
*A61B 1/018* (2006.01)
*A61B 17/00* (2006.01)

(52) U.S. Cl.
CPC .......... *A61B 1/00133* (2013.01); *A61B 1/018* (2013.01); *A61B 2017/0034* (2013.01); *A61B 2017/2212* (2013.01); *A61B 2017/2217* (2013.01)

(56) References Cited

U.S. PATENT DOCUMENTS

| | | |
|---|---|---|
| 6,093,196 A | 7/2000 | Okada |
| 2003/0153944 A1 | 8/2003 | Phung et al. |
| 2005/0075648 A1 | 4/2005 | Komiya |
| 2010/0222806 A1 | 9/2010 | Phung et al. |
| 2014/0012283 A1 | 1/2014 | Yasuda et al. |
| 2016/0242795 A1 | 8/2016 | Iwabuchi et al. |

FOREIGN PATENT DOCUMENTS

| | | |
|---|---|---|
| EP | 3 069 668 A1 | 9/2016 |
| GB | 2066668 A | 7/1981 |
| JP | S61-106145 A | 5/1986 |
| JP | S62-42617 B2 | 9/1987 |
| JP | 3075355 B2 | 8/2000 |
| JP | 2002-253559 A | 9/2002 |
| JP | 2004-188011 A | 7/2004 |
| JP | 2005-087398 A | 4/2005 |
| JP | 4694010 A | 6/2011 |
| JP | 2015-009003 A | 1/2015 |
| WO | 2004/062513 A1 | 7/2004 |
| WO | WO 2012/141213 A1 | 10/2012 |
| WO | 2015/072394 A1 | 5/2015 |

OTHER PUBLICATIONS

International Search Report dated Aug. 9, 2016 issued in PCTJP2016/065640.

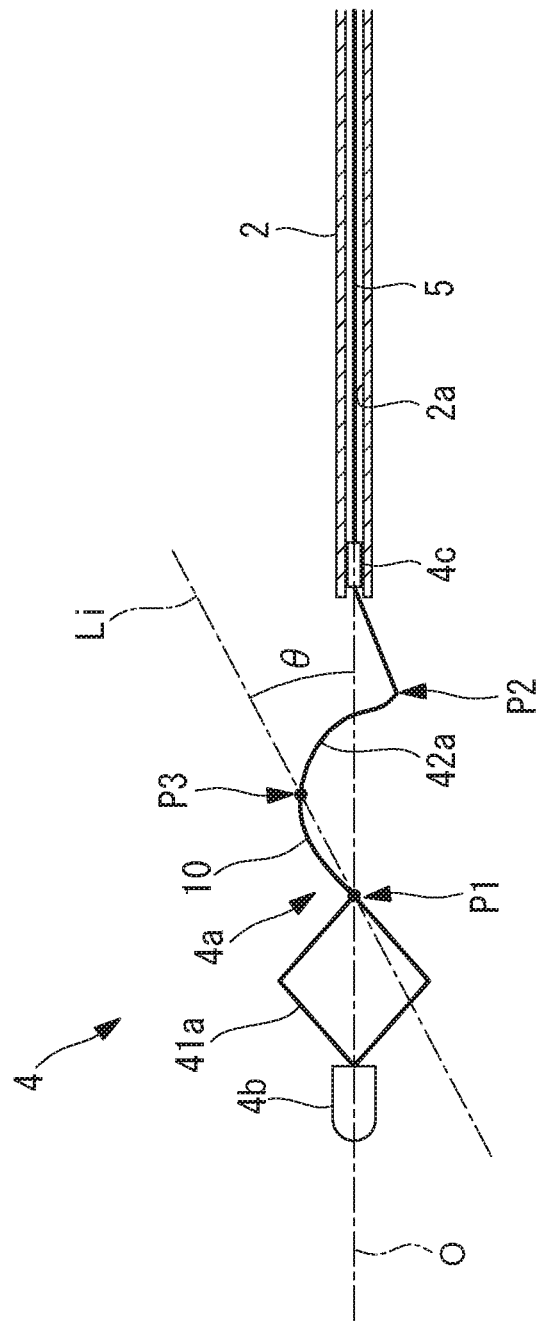

ENDOSCOPE TREATMENT TOOL

CROSS-REFERENCE TO RELATED APPLICATIONS

This is a continuation of International Application PCT/JP2016/065640, with an international filing date of May 26, 2016, which is hereby incorporated by reference herein in its entirety.

TECHNICAL FIELD

The present invention relates to an endoscope treatment tool.

BACKGROUND ART

There are known basket-type gripping forceps for ejecting a gallstone formed in the bile duct from the bile duct (for example, refer to Patent Literature 1 and Patent Literature 2). Such basket-type gripping forceps include a basket section formed into a basket shape by binding a plurality of wires at both sides thereof. A gallstone can be ejected from the bile duct by taking the gallstone into the basket section via a gap between wires of the basket section when spread out in the bile duct and then extracting the basket section as a whole from the bile duct.

CITATION LIST

Patent Literature

{PTL 1}
Publication of Japanese Patent No. 3075355
{PTL 2}
Japanese Examined Patent Application, Publication No. 62-42617

SUMMARY OF INVENTION

One aspect of the present invention is an endoscope treatment tool including: a sheath having a lumen extending along a longitudinal axis; a basket section that protrudes from the lumen of the sheath and that has at least one elastic wire; and an operating wire for advancing/retracting the basket section in a longitudinal direction of the sheath, wherein one of the elastic wires has: a maximum outer diameter section at which an outer diameter of the basket section is largest between a distal end of the elastic wire and a proximal end of the elastic wire; a first maximum section that, in a lateral view from a direction orthogonal to a normal from the maximum outer diameter section to a central axis of the basket section, is largest on the opposite side of the central axis from the maximum outer diameter section between the maximum outer diameter section and the proximal end of the elastic wire; and a second maximum section that is largest at a position away from the normal between the maximum outer diameter section and the first maximum section, and in a front view of the basket section, the first maximum section is located on the opposite side of a straight line, which is orthogonal to the normal at the central axis, from the maximum outer diameter section side.

BRIEF DESCRIPTION OF DRAWINGS

FIG. 5B is a side view showing the shape of the elastic wire in FIG. 4 in a lateral view in a direction along the normal from the maximum outer diameter section to the central axis.

DESCRIPTION OF EMBODIMENTS

An endoscope treatment tool 1 according to one embodiment of the present invention will now be described with reference to the drawings.

Figure 1:
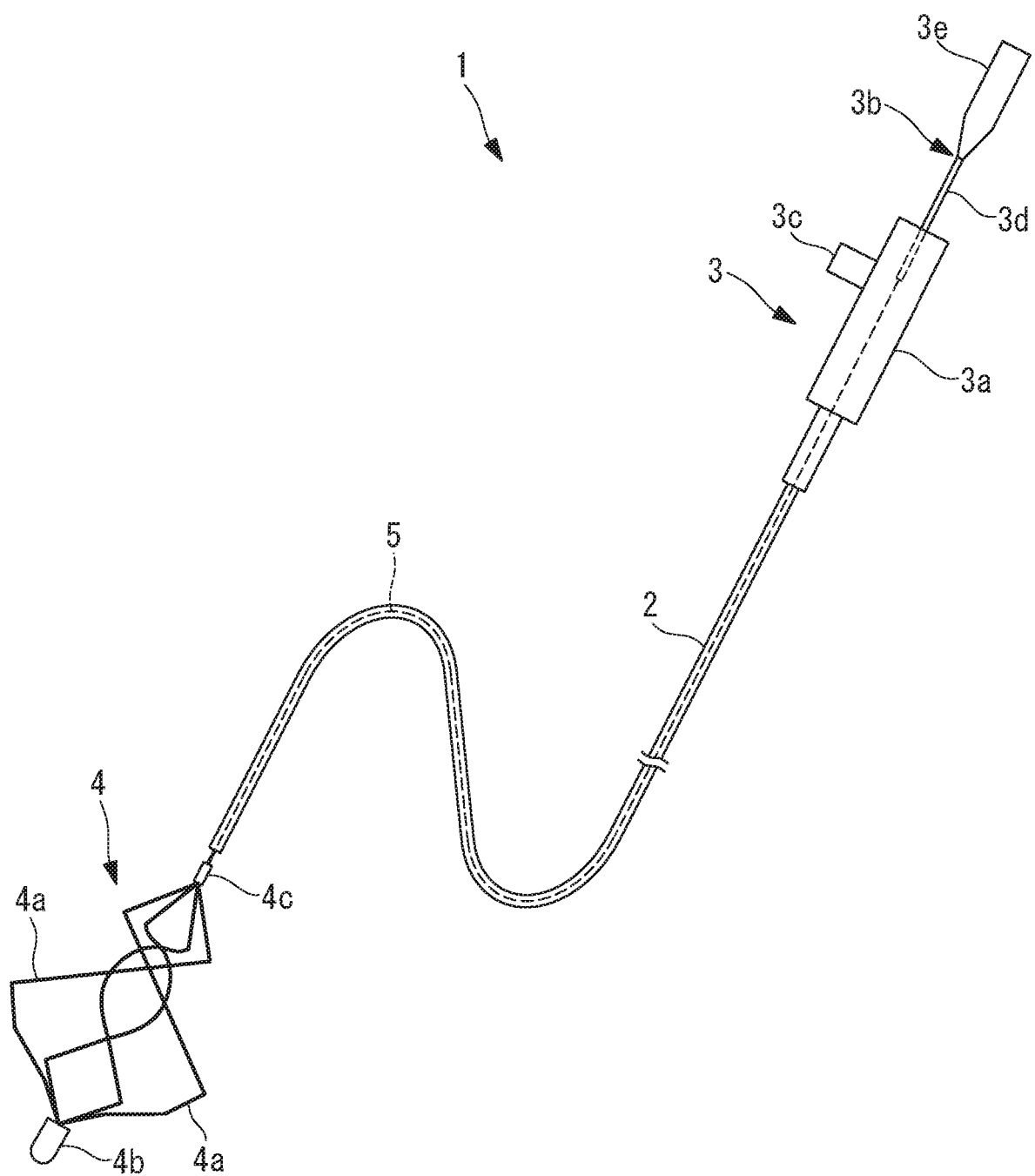
FIG. 1 is an overall configuration diagram showing an endoscope treatment tool according to one embodiment of the present invention.
Figure 2:
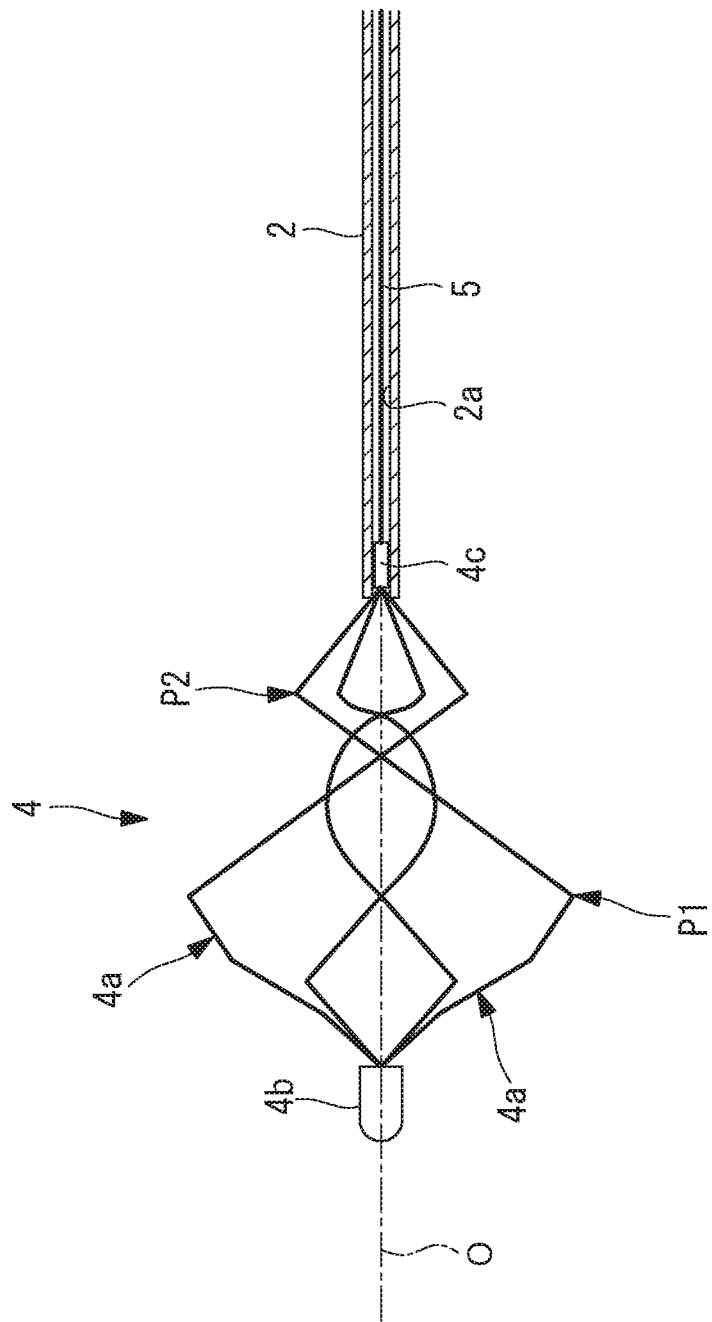
FIG. 2 is a longitudinal sectional view showing an expanded form of a basket section of the endoscope treatment tool in FIG. 1.

The endoscope treatment tool 1 according to this embodiment is a treatment tool that is introduced into the body via a channel (not shown in the figure) of an endoscope and, as shown in FIGS. 1 and 2, includes: an elongated sheath 2 having flexibility; an operating section 3 provided on the proximal end side of the sheath 2; a basket section 4 disposed on the distal end side of the sheath 2; and an operating wire 5 for advancing/retracting the basket section 4 in the longitudinal direction of the sheath 2 via the operation of the operating section 3.

The sheath 2 has an outer diameter that allows the sheath 2 to be inserted into the channel of the endoscope and, as shown in FIG. 2, includes a lumen 2a passing therethrough in the longitudinal direction. For the material of the sheath 2, a known resin material, such as a fluoroethylene resin or a thermoplastic elastomer, a coil sheath formed by winding a metal material, or a braid using a metal wire can be selected, as appropriate, or combined for employment.

The operating section 3 includes: an operating section main body 3a; and a slider 3b movable in the longitudinal direction of the sheath 2 relative to the operating section main body 3a. In the figure, reference sign 3c denotes a liquid feeding port that is provided in the operating section main body 3a and that communicates with the lumen 2a in the sheath 2. The liquid feeding port 3c can have a syringe and a pump, not shown in the figure, connected thereto.

The slider 3b includes a shaft 3d to which the proximal end of the operating wire 5 is fixed and a grip 3e fixed to the shaft 3d. When an operator grips the grip 3e and pulls it towards the proximal end side relative to the operating section main body 3a, the traction force is transmitted to the operating wire 5, and the basket section 4 on the distal end of the operating wire 5 is retreated towards the proximal end side. In contrast, when the operator grips the grip 3e and pushes it towards the distal end side relative to the operating section main body 3a, the pushing force towards the distal end side is transmitted to the operating wire 5, thereby moving forward the basket section 4 on the distal end of the operating wire 5 towards the distal end side.

Figure 3:
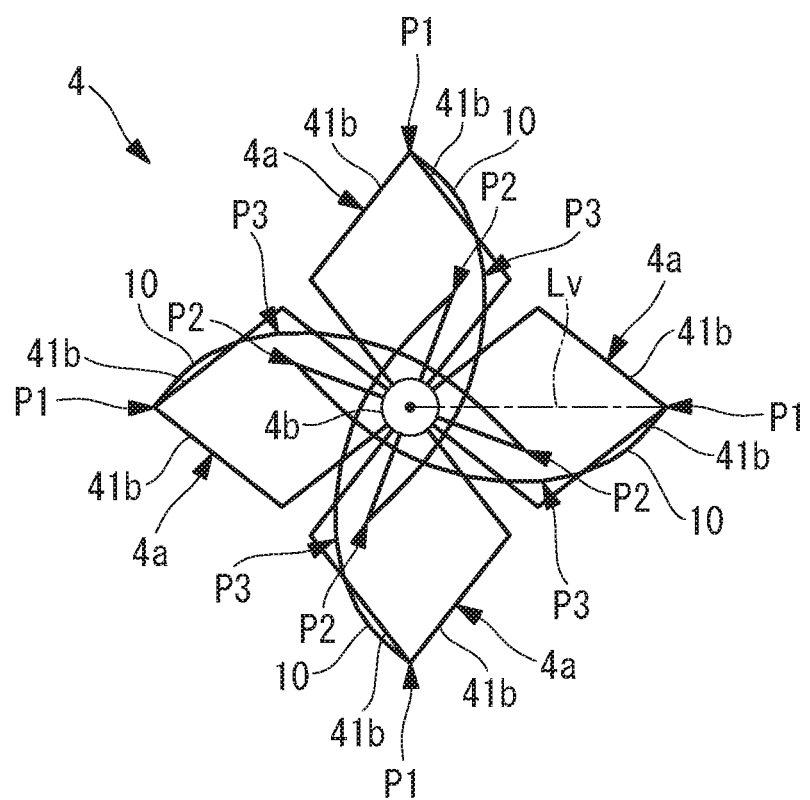
FIG. 3 is a front view of the basket section in FIG. 2, as seen from a direction along a central axis.

As shown in FIGS. 2 and 3, the basket section 4 is formed into the shape of a basket, which is capable of contracting and expanding in the radial direction, by binding a plurality of elastic wires 4a that are arranged in a manner spaced apart from one another in the circumferential direction at both ends (distal end and proximal end) thereof with a distal-end binding section (binding section) 4b and a proximal-end binding section 4c. More specifically, the basket section 4 is configured to be capable of shifting between a contraction mode, in which the basket section 4 contracts in the radial direction and can be accommodated in the lumen 2a of the sheath 2, and an expansion mode, in which, as shown in FIG. 2, the basket section 4 expands outwardly in the radial direction due to an elastic force (resilient force) thereof in a state free from external forces that reduce the diameter of the basket section 4 as a result of the basket section 4 protruding forward via an opening at the distal end of the lumen 2a.

The elastic wires 4a constituting the basket section 4 are formed of a material having high elasticity, such as a super elastic alloy, in the form of a single wire or twisted wires. Such a super elastic alloy includes, for example, a nickel titanium alloy.

Figure 4:
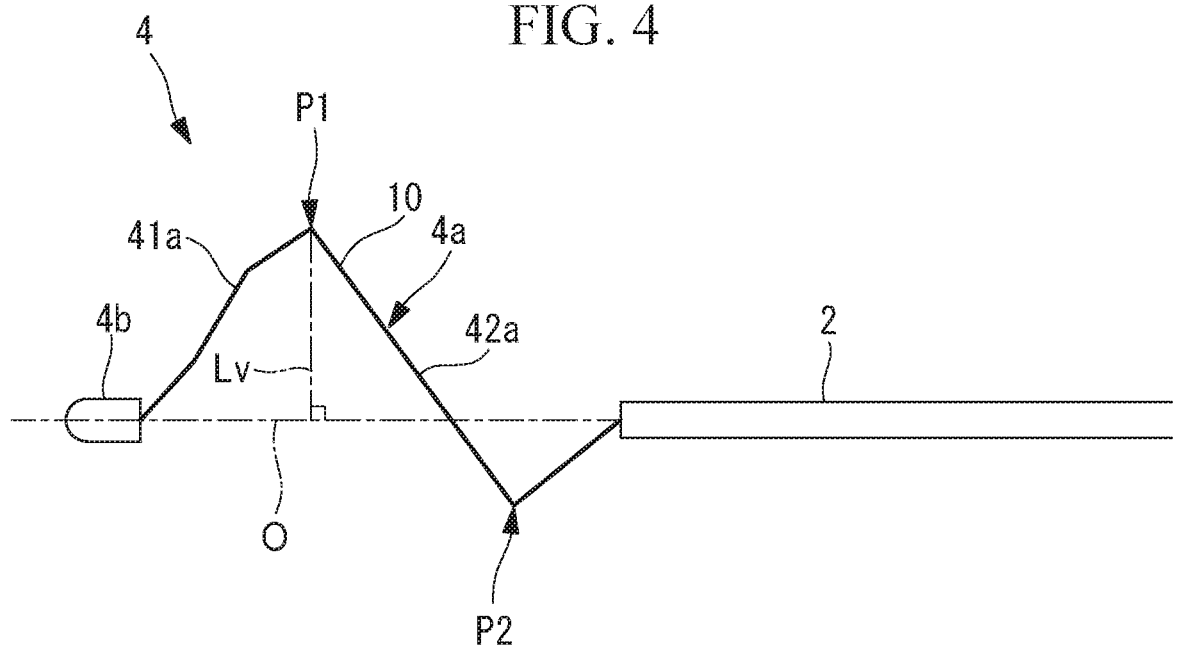
FIG. 4 is a side view showing the shape of one of the elastic wires constituting the basket section in FIG. 2 in a lateral view orthogonal to a normal from a maximum outer diameter section of the elastic wire to the central axis.

In this embodiment, the basket section 4 has a maximum outer diameter section P1, at which the outer diameter of the basket section 4 is largest, between the distal end and the proximal end of each of the elastic wires 4a, as shown in FIG. 2 and FIG. 4, which depicts only one of the elastic wires 4a constituting the basket section 4. The maximum outer diameter sections P1 are located on the distal end side of the basket section 4. In addition, in a front view of FIG. 3, as shown in FIG. 4 depicting a lateral view orthogonal to a normal Lv from a maximum outer diameter section P1 to a central axis O of the basket section 4, each of the elastic wires 4a has a first maximum section P2 that is largest on the opposite side of the central axis O from the maximum outer diameter section P1.

The first maximum sections P2 are each a bent section formed by bending the wire so as to project outwardly in the radial direction and are located in a manner spaced apart from the maximum outer diameter sections P1 to the proximal end side between the maximum outer diameter sections P1 and the proximal ends of the elastic wires 4a. Note that the first maximum section P2 does not necessarily take the shape formed by bending the wire so as to project outwardly in the radial direction. Instead of this, the first maximum section P2 may take a shape formed by smoothly curving the wire so as to bulge outwardly in the radial direction.

Figure 5A:
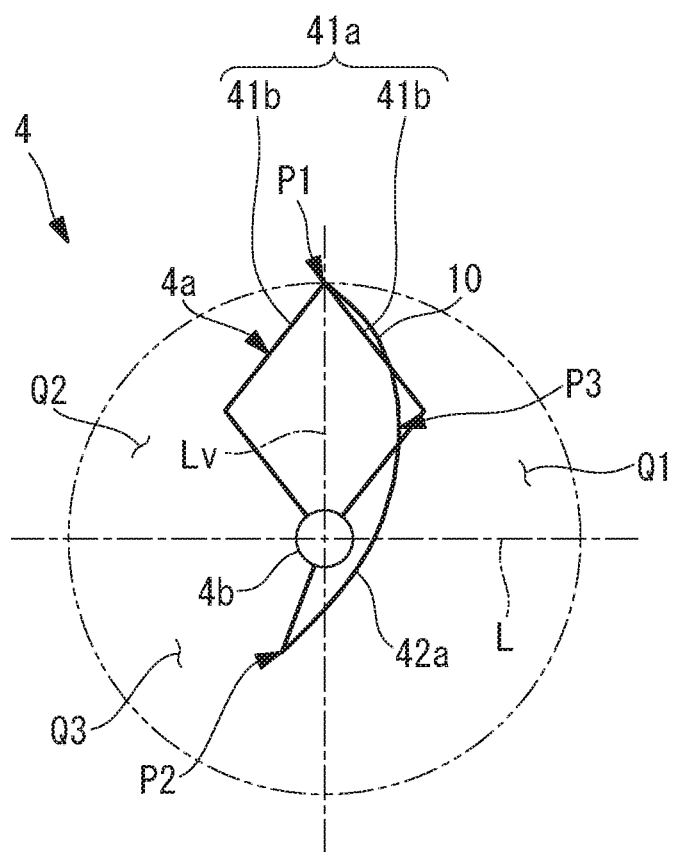
FIG. 5A is a front view showing the shape of the elastic wire in FIG. 4.

Furthermore, as shown in FIG. 5A depicting a front view as seen in a direction along the central axis O of the basket section 4 from the distal-end binding section 4b, each of the elastic wires 4a includes a second maximum section P3 that is largest on the opposite side of the normal Lv from the first maximum sections P2. As shown in FIG. 5B, in a lateral view from a direction along the normal Lv shown in FIG. 5A, the second maximum section P3 is preferably located at a position in which an angle θ between the central axis O and a straight line Li connecting the second maximum section P3 and the maximum outer diameter section P1 satisfies $0° < \theta \leq 90°$.

Furthermore, as shown in FIG. 5A, each of the elastic wires 4a extends from the maximum outer diameter section P1 to the first maximum section P2 so as to intersect a straight line L, which is orthogonal to the normal Lv at the central axis O (center of the distal-end binding section 4b) thereof.

In other words, in the front view shown in FIG. 5A, the first maximum section P2 is located on the opposite side of the straight line L from the maximum outer diameter section P1. It is more preferable that, in a rectangular coordinate system defined by two straight lines (straight line L and normal Lv) orthogonal to the central axis O in the front view, as shown in FIG. 5A, the first maximum section P2 be located in a third quadrant Q3 and the second maximum section P3 be located in a first quadrant Q1 when the maximum outer diameter section P1 is located on the boundary between the first quadrant Q1 and a second quadrant Q2.

As shown in FIG. 4, each of the elastic wires 4a has: a first portion 41a extending from the distal end of the elastic wire 4a to the maximum outer diameter section P1; and a second portion 42a that continues from the first portion 41a and that extends to the first maximum section P2 via the second maximum section P3. As shown in FIG. 5A, the first portion 41a is formed into a substantially rhombic shape by two bent elastic wires 41b from the distal end towards the maximum outer diameter section P1 so as to gradually increase the diameter in the radial direction of the basket section 4.

The second portion 42a reduces the diameter as it extends from the maximum outer diameter section P1 towards the first maximum section P2. In addition, in the lateral view as shown in FIG. 4, the elastic wire 4a is bent in a substantially Z shape between the distal end and the proximal end of the elastic wire 4a, and the maximum outer diameter section P1 and the first maximum section P2 protrude in the opposite directions to each other with respect to the central axis O.

Figure 6:
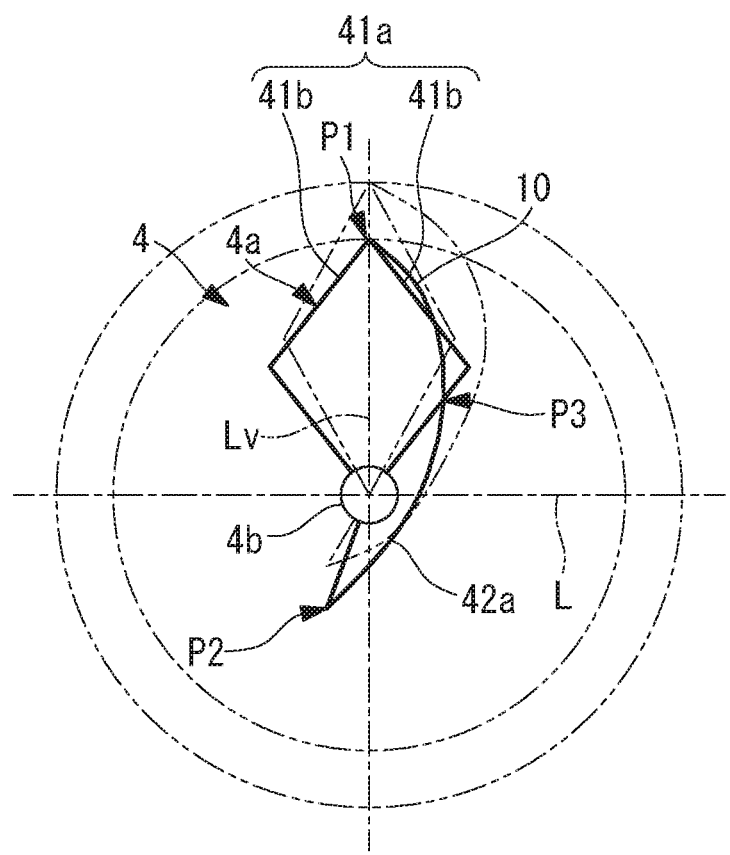
FIG. 6 is a front view showing the comparison of states before and after radially outward movement of the maximum outer diameter section of the elastic wire in FIG. 5.

Regarding the basket section 4, as shown in FIG. 6, as a result of, for example, the proximal end side of the basket section 4 (end side more proximal than the second portion 42a) being partially housed in the sheath 2 according to a traction force produced by the operating wire 5, the first maximum section P2 approaches the central axis O of the basket section 4. As the operating wire 5 is pulled and the portion up to the first maximum section P2 is housed in the sheath 2, the maximum outer diameter section P1 is pushed by the second portion 42a outwardly in the radial direction and is shifted as indicated by two-dot chain lines in FIG. 6.

In this embodiment, in the first portions 41a, eight elastic wires 41b are arranged in a manner spaced apart from one another in the circumferential direction, and in the other portions, four elastic wires 4a are arranged in a manner spaced apart from one another in the circumferential direction. As shown in FIG. 3, the first maximum sections P2 of the four elastic wires 4a are located so as to be shifted by 90° relative to one another in the circumferential direction. Likewise, the second maximum sections P3 are also located so as to be shifted by 90° relative to one another in the circumferential direction.

The operation of the endoscope treatment tool 1 according to this embodiment with the above-described structure will be described below.

Figure 8:
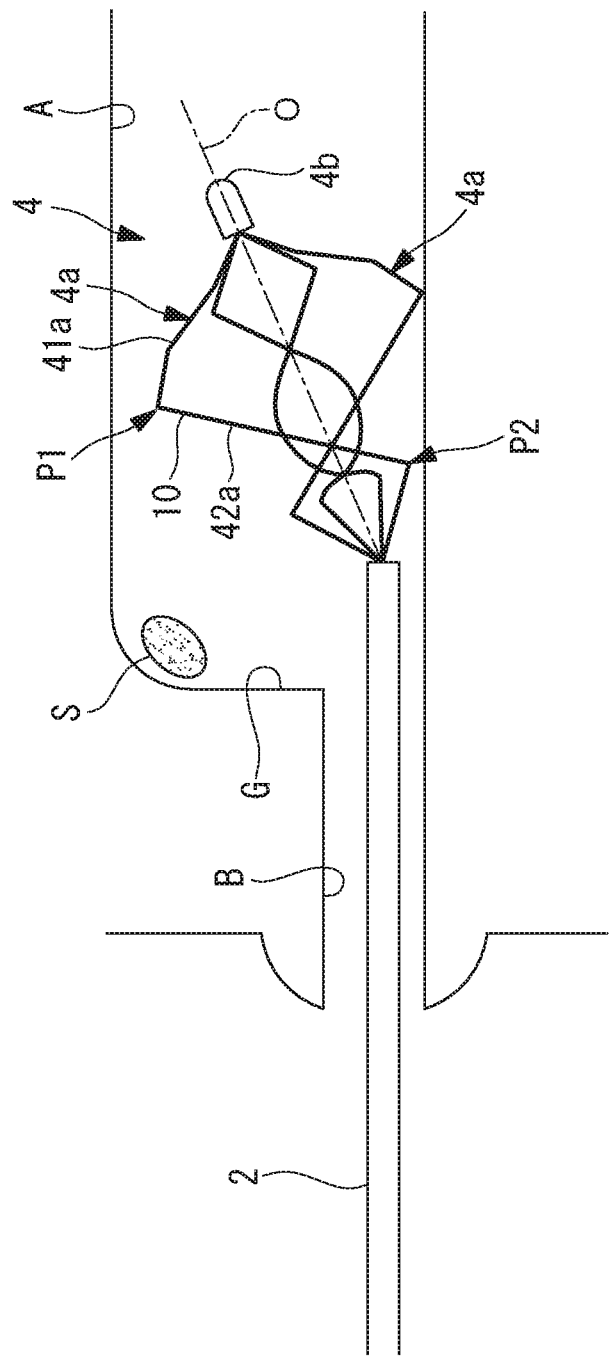
FIG. 8 is a diagram showing a state where the basket section of the endoscope treatment tool in FIG. 1 is expanded in a bile duct.
Figure 9:
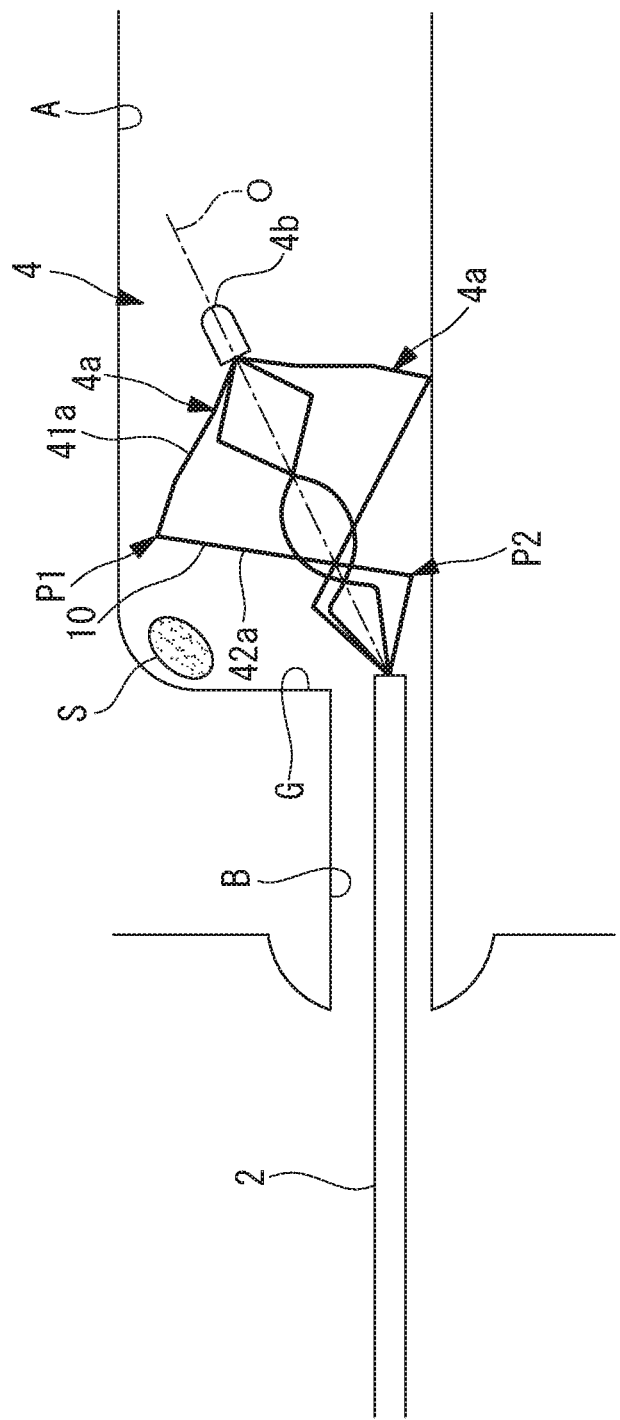
FIG. 9 is a diagram showing a state where a portion of the basket section in FIG. 8 is extracted from the bile duct.
Figure 10:
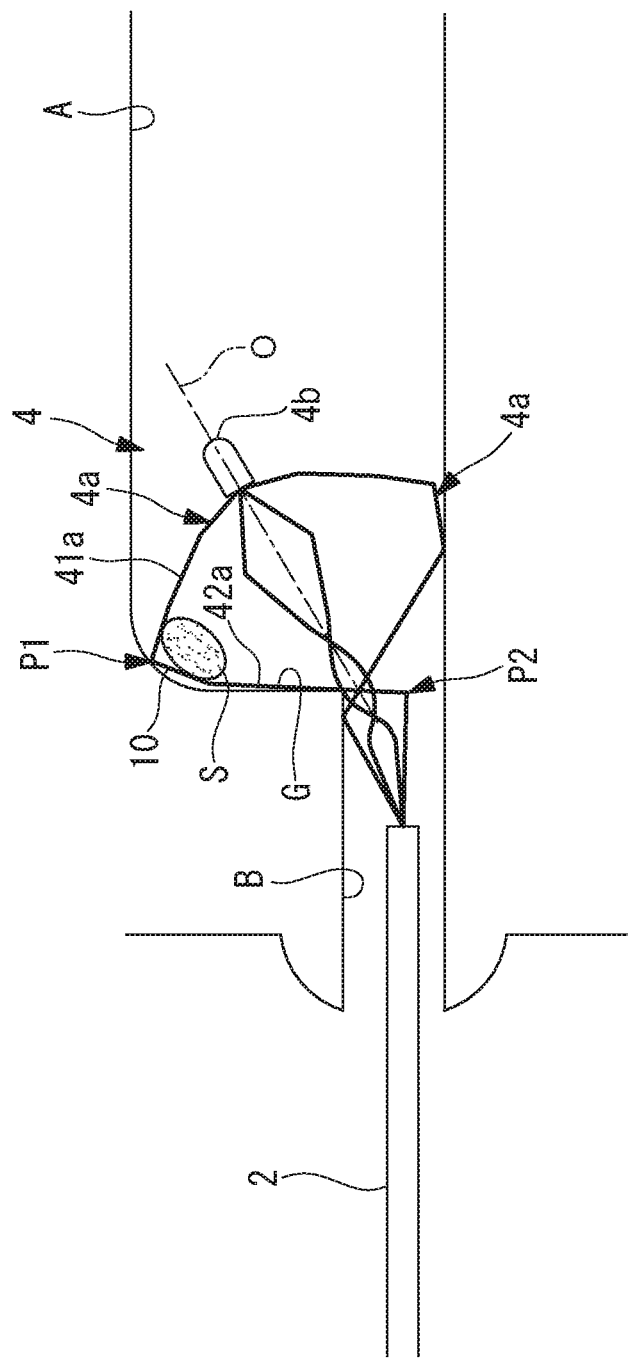
FIG. 10 is a diagram showing a state where the gallstone is caught by extracting the basket section in FIG. 9 until the first maximum section is out of the bile duct.

The following description assumes a case in which a gallstone S in a bile duct A is caught using the endoscope treatment tool 1 according to this embodiment and, as shown in FIGS. 8 to 10, a case in which a small gallstone S present in a stepped portion G obliquely formed at the boundary between the bile duct A and a duodenal papilla B is caught.

The basket section 4 is housed in the sheath 2 in a contracted state, and then the distal end of the sheath 2 is inserted into the bile duct A via the duodenal papilla B through a channel of the endoscope that has been inserted into the duodenum. A pressing force is applied to the operating wire 5 by moving forward the slider 3b of the operating section 3 in this state, and the basket section 4 is protruded via the opening of the lumen 2a located at the distal end of the sheath 2.

As shown in FIG. 8, when released in the wide bile duct A, the basket section 4 is restored to an expanded state by an elastic resilient force, thus taking a basket shape having the maximum outer diameter sections P1 and the first maximum sections P2. Since the bile duct A is wide on the stepped portion G side and narrow on the opposite side, the basket section 4 restored to an expanded state, as shown in FIG. 8, is placed into a state where the basket section 4 is separated from an inner wall of the bile duct A on the stepped portion G side and is in contact with an inner wall of the bile duct A on the opposite side.

By pulling the sheath 2 and the operating wire 5 towards the proximal end side in this state, the basket section 4 is moved to the proximal end side in the bile duct A. By doing so, as shown in FIG. 9, the proximal end side of the basket section 4 is pulled into a narrow passage of the duodenal papilla B, and the basket section 4 is gradually contracted inwardly in the radial direction, starting at the proximal end side.

More specifically, the proximal end side of the basket section 4 (end side more proximal than the second portion 42a) is partially pulled into the narrow passage of the duodenal papilla B, whereby the proximal end side of the basket section 4 is subjected to an external force from the duodenal papilla B, causing the first maximum sections P2 to approach the central axis O of the basket section 4.

When the first maximum sections P2 approach the central axis O of the basket section 4, the second portions 42a (the elastic wires extending between the maximum outer diameter sections P1 and the first maximum sections P2) are urged by elastic forces of the elastic wires 4a themselves in a direction crossing the straight line L so as to further increase the maximum outer diameter of the basket section 4 (maximum outer diameter in the above-described expanded state), thereby causing the maximum outer diameter sections P1 to move outwardly in the radial direction, as shown in FIGS. 6 and 10.

Note that, in the basket section 4, the maximum outer diameter sections P1 preferably move farther outward in the radial direction as the first maximum sections P2 more closely approach the central axis O of the basket section 4.

For this purpose, the basket section 4 is tilted towards the stepped portion G side by a reaction force produced by the inner wall of the bile duct A on the opposite side from the stepped portion G. More specifically, as shown in FIG. 10, as a result of an increase in diameter due to the maximum outer diameter sections P1 and tilting of the entire basket section 4, the basket section 4 reaches the small gallstone S present in the stepped portion G.

Figure 7:
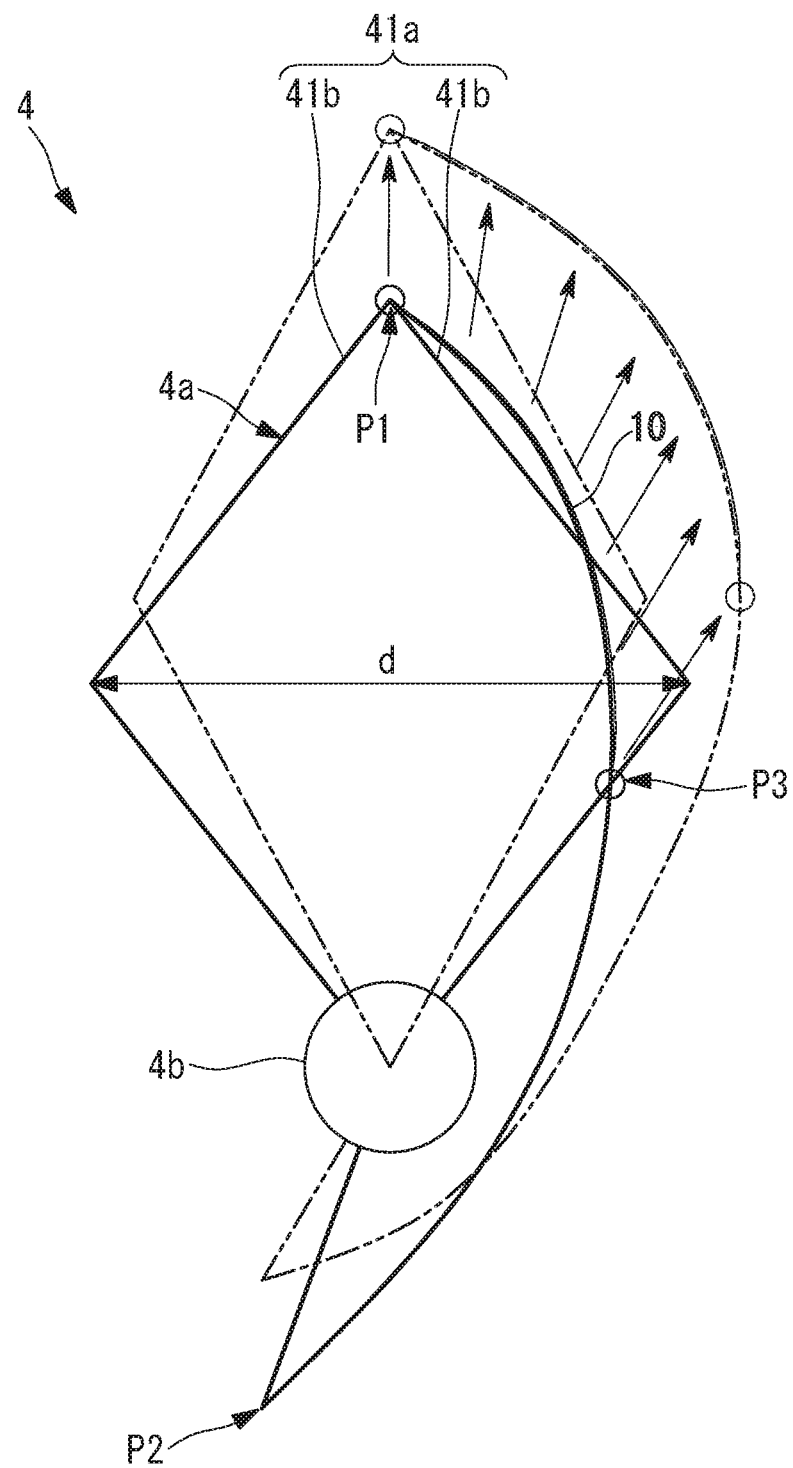
FIG. 7 is a partial expanded view for illustrating detailed movement of the elastic wire in FIG. 6.

In this case, as shown in FIG. 10, according to the endoscope treatment tool 1 of this embodiment, a portion from the maximum outer diameter section P1 in any one of the elastic wires 4a to a vicinity of the second maximum section P3 (hereinafter, referred to as a catch section) 10 is disposed in the vicinity of the surface of the stepped portion G in which the small gallstone S is present. Along with this, the basket section 4 is disposed so that the central axis O of the basket section 4 is tilted relative to the central axis of the bile duct A. Note that, at this time, the central axis O of the basket section 4 is also tilted relative to the longitudinal axis of the sheath 2. When the maximum outer diameter sections P1 move outwardly in the radial direction as a result of the first maximum sections P2 approaching the central axis O, the catch section 10 moves in a direction intersecting the longitudinal axis of the elastic wire 4a, as shown in FIG. 7 (direction indicated by the arrows in FIG. 7). More specifically, since the catch section 10 moves so as to pass across between the small gallstone S and the stepped portion G, the small gallstone S is caught and scooped from the stepped portion G by the elastic wire 4a at this portion.

Thereafter, the scooped gallstone S is caught, without fail, by the eight elastic wires 41b of the first portions 41a, which are arranged with a smaller gap interposed therebetween on the distal end side of the basket section 4.

By doing so, the gallstone S can be accommodated in the basket section 4, and the basket section 4 is contracted so as to be smaller than the inner diameter of the duodenal papilla B by further pulling the sheath 2 and the operating wire 5. Thus, the gallstone S wrapped by the basket section 4 can be ejected from the bile duct A.

In this case, as shown in FIG. 7, it is preferable that, between the distal ends and the maximum outer diameter sections P1 of the elastic wires 4a, the maximum width d of the space between neighboring elastic wires 4a be set to be smaller than the length along an elastic wire 4a from the maximum outer diameter section P1 to the second maximum section P3. By doing so, it is possible to suppress widening of the gap between neighboring wires 41b of the plurality of elastic wires 41b, whereby the large gallstone S caught by the catch section 10 does not easily drop from within the basket section 4.

In this manner, the endoscope treatment tool 1 according to this embodiment affords an advantage in that the small gallstone S present in the stepped portion G obliquely formed at the boundary between bile duct A and the duodenal papilla B can be caught and ejected more reliably.

Figure 11:
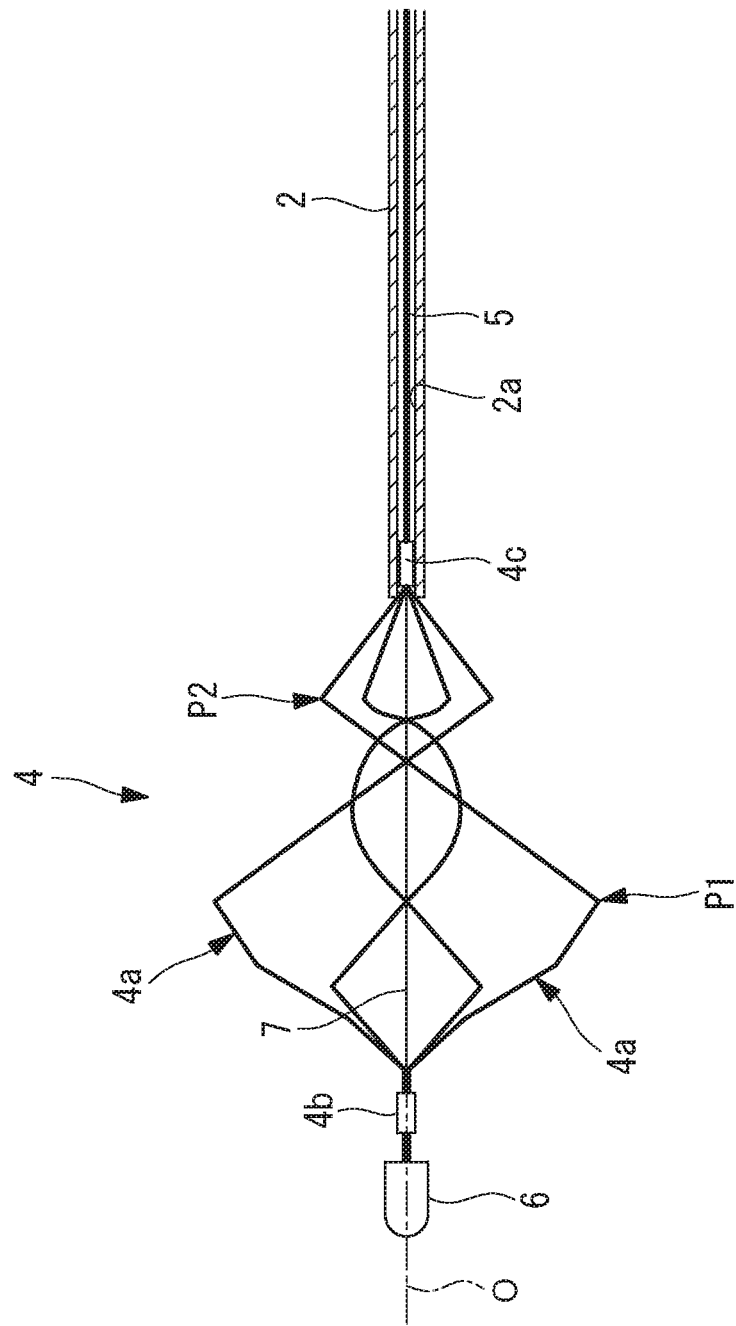
FIG. 11 is a side view showing a modification of the basket section in FIG. 2.

Note that in this embodiment, as shown in FIG. 11, a distal-end tip 6 may be provided at a site more distal than the distal-end binding section 4b, and a support member 7, at least a part of which is inserted into the sheath 2 via the basket section 4, may be fixed to the distal-end tip 6. The support member 7 has higher rigidity than the elastic wires 4a, can support the basket section 4, and can preserve the shape of the basket section 4. In addition, when the basket section 4 is pushed by the inner wall of the bile duct A, the basket section 4 can be titled by allowing the support member 7 to bend towards the stepped portion G side.

The support member 7 is preferably disposed at a position displaced from the central axis O of the basket section 4.

By doing so, when the gallstone S is caught by the basket section 4, the gallstone S can be disposed in the vicinity of the central axis O of the basket section 4 by pushing aside the support member 7 outwardly in the radial direction relative to the central axis O. Since the gaps between the elastic wires 4a become small on the distal end side or the proximal end side where the elastic wires 4a converge near the central axis O, the risk of dropping the gallstone S from the basket section 4 can be reduced by disposing the gallstone S in the vicinity of the central axis O.

Figure 12:
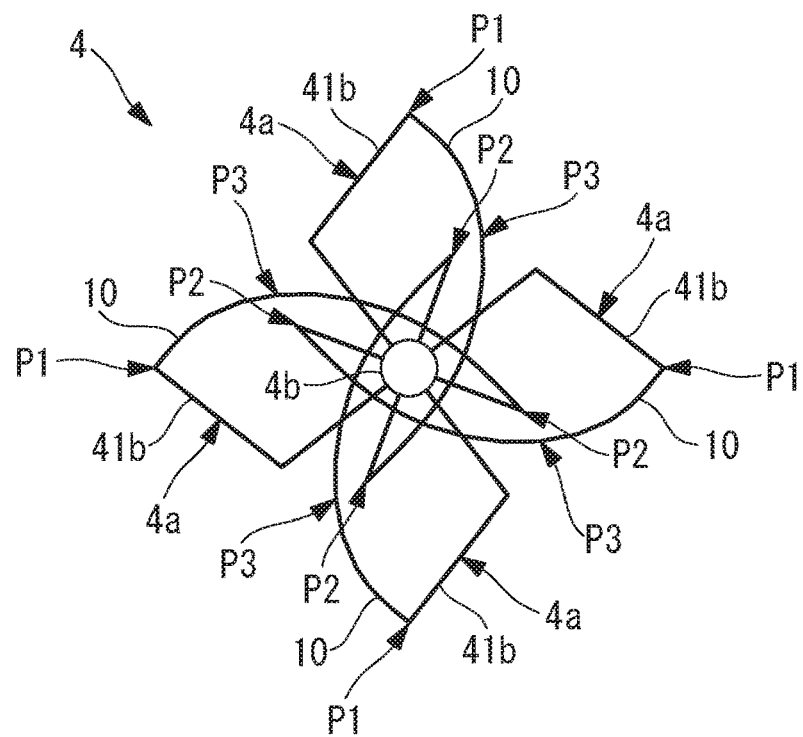
FIG. 12 is a front view showing a modification of the basket section in FIG. 2.
Figure 13:
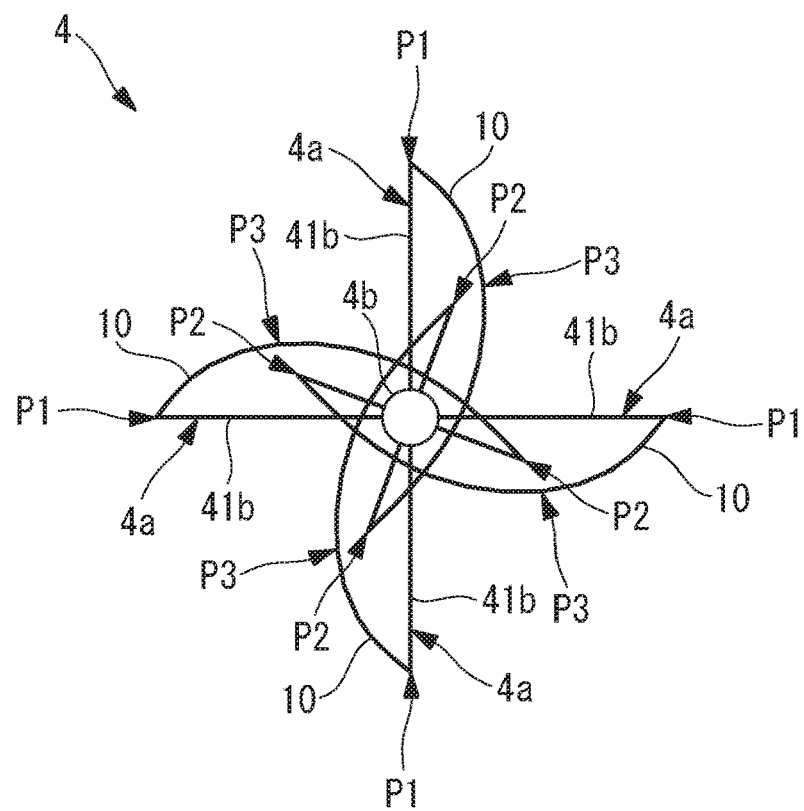
FIG. 13 is a front view showing a modification of the basket section in FIG. 2.

In addition, although this embodiment has been described by way of an example where each of the elastic wires 4a is split into two elastic wires 41b in the first portion 41a, instead of this, elastic wires 4a that are not split, as shown in FIG. 12, may be employed. Furthermore, as shown in FIG. 13, in a front view, the basket section 4 may employ a shape in which the elastic wire 4a of each of the first portions 41a linearly extends in the radial direction.

Figure 14:
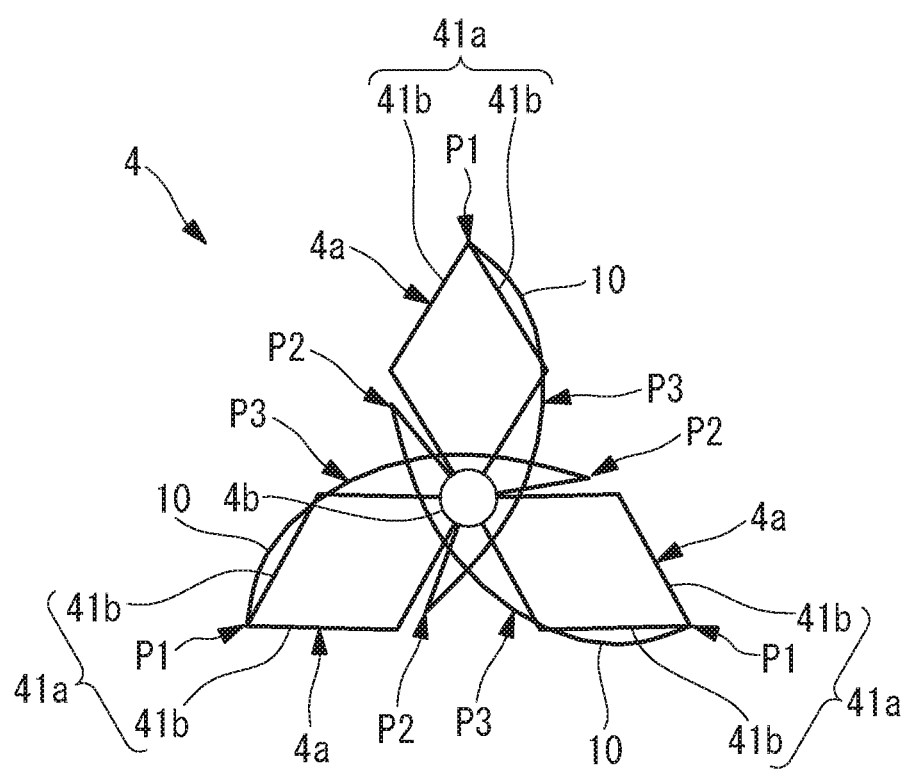
FIG. 14 is a front view showing a modification of the basket section in FIG. 2.

In addition, although this embodiment has been described by way of an example where the basket section 4 is formed of the four elastic wires 4a with gaps interposed therebetween in the circumferential direction, instead of this, the basket section 4 may be formed of three elastic wires 4a, or alternatively, the basket section 4 may be formed of five or more elastic wires 4a, as shown in FIG. 14.

As a result, the above-described embodiment leads to the following aspect.

One aspect of the present invention is an endoscope treatment tool including: a sheath having a lumen extending along a longitudinal axis; a basket section that protrudes from the lumen of the sheath and that has at least one elastic wire; and an operating wire for advancing/retracting the basket section in a longitudinal direction of the sheath, wherein one of the elastic wires has: a maximum outer diameter section at which an outer diameter of the basket section is largest between a distal end of the elastic wire and a proximal end of the elastic wire; a first maximum section that, in a lateral view from a direction orthogonal to a normal from the maximum outer diameter section to a central axis of the basket section, is largest on the opposite side of the central axis from the maximum outer diameter section between the maximum outer diameter section and the proximal end of the elastic wire; and a second maximum section that is largest at a position away from the normal between the maximum outer diameter section and the first maximum section, and in a front view of the basket section, the first maximum section is located on the opposite side of a straight line, which is orthogonal to the normal at the central axis, from the maximum outer diameter section side.

In the above-described aspect, in the front view of the basket section, the second maximum section may be largest on the opposite side of the normal from the first maximum section, and the first maximum section, the second maximum section, and the maximum outer diameter section may be arranged sequentially from the proximal end side towards the distal end side of the basket section.

In the above-described aspect, a region between the second maximum section and the maximum outer diameter section may have a catch section for catching a gallstone in a state where the central axis of the basket section is tilted relative to a central axis of a bile duct.

In the above-described aspect, when the first maximum section is made to approach the central axis, a region from the second maximum section to the maximum outer diameter section may move in a direction away from the central axis, and the maximum outer diameter section may move in a direction away from the central axis.

In the above-described aspect, a plurality of the elastic wires may be arranged in a circumferential direction about the central axis of the basket section, and the second maximum sections of the elastic wires may be arranged at positions displaced in the circumferential direction.

In the above-described aspect, from the distal ends of the elastic wires to the maximum outer diameter sections, a maximum width of the space between neighboring elastic wires of the plurality of the elastic wires may be set to be smaller than lengths, along the elastic wires, from the maximum outer diameter sections to the second maximum sections.

In the above-described aspect, the first maximum section may be a bent section formed by bending the elastic wire.

In the above-described aspect, in a lateral view from a direction along the normal, an angle θ between the central axis and a straight line connecting the second maximum section and the maximum outer diameter section is $0° < θ ≤ 90°$.

The present invention affords an advantage in that even a gallstone trapped in a stepped portion obliquely formed at the boundary between the bile duct and the duodenal papilla can be more reliably caught and ejected.

REFERENCE SIGNS LIST

1 Endoscope treatment tool
2 Sheath
2a Lumen
4 Basket section
4a Elastic wire
4b Distal-end binding section (binding section)
5 Operating wire
10 Catch section
P1 Maximum outer diameter section
P2 First maximum section
P3 Second maximum section
S Gallstone

The invention claimed is:

1. An endoscope treatment tool comprising:
   a sheath having a lumen extending along a longitudinal axis;
   a basket section that protrudes from the lumen of the sheath and that has at least one elastic wire; and
   an operating wire for advancing/retracting the basket section in a longitudinal direction of the sheath,
   wherein one of the elastic wires has: a maximum outer diameter section at which an outer diameter of the basket section is largest between a distal end of the elastic wire and a proximal end of the elastic wire; a first maximum section that, in a lateral view from a direction orthogonal to a normal from the maximum outer diameter section to a central axis of the basket section, is largest on the opposite side of the central axis from the maximum outer diameter section between the maximum outer diameter section and the proximal end of the elastic wire; and a second maximum section that, in a front view of the basket section, is largest on the opposite side of the normal from the first maximum section, and
   in the front view of the basket section having first, second, third and fourth quadrants arranged counterclockwise around the central axis, the maximum outer diameter section is located outside of the third and fourth quadrants, the second maximum section is located in the first quadrant and the first maximum section is located in the third quadrant.

2. The endoscope treatment tool according to claim 1, wherein
   the first maximum section, the second maximum section, and the maximum outer diameter section are arranged sequentially from the proximal end side towards the distal end side of the basket section.

3. The endoscope treatment tool according to claim 1, wherein a region between the second maximum section and the maximum outer diameter section has a catch section for catching a gallstone in a state where the central axis of the basket section is tilted relative to a central axis of a bile duct.

4. The endoscope treatment tool according to claim 1, wherein, when the first maximum section is made to approach the central axis, a region from the second maximum section to the maximum outer diameter section moves in a direction away from the central axis and the maximum outer diameter section moves in a direction away from the central axis.

5. The endoscope treatment tool according to claim 1, wherein a plurality of the elastic wires are arranged in a circumferential direction about the central axis of the basket section, and the second maximum sections of the elastic wires are arranged at positions displaced in the circumferential direction.

6. The endoscope treatment tool according to claim 5, wherein, from the distal ends of the elastic wires to the maximum outer diameter sections, a maximum width of the space between neighboring elastic wires of the plurality of the elastic wires is set to be smaller than lengths, along the elastic wires, from the maximum outer diameter sections to the second maximum sections.

7. The endoscope treatment tool according to claim 1, wherein the first maximum section is a bent section formed by bending the elastic wire.

8. The endoscope treatment tool according to claim 1, wherein in a lateral view from a direction along the normal, an angle $\theta$ between the central axis and a straight line connecting the second maximum section and the maximum outer diameter section is $0°<\theta\leq90°$.

9. The endoscope treatment tool according to claim 1, wherein, in the front view of the basket section, the elastic wire between the distal end of the elastic wire and the maximum outer diameter section is formed in a rhombic shape.

\* \* \* \* \*